United States Patent [19]

Seidy

[11] Patent Number: 5,125,918
[45] Date of Patent: * Jun. 30, 1992

[54] SANITARY NAPKIN HAVING AN ATTACHMENT SYSTEM COMPRISING BIASED HINGES

[75] Inventor: Wassim Seidy, Somerset, N.J.

[73] Assignee: McNeil-PPC, Inc., Milltown, N.J.

[ * ] Notice: The portion of the term of this patent subsequent to Mar. 27, 2007 has been disclaimed.

[21] Appl. No.: 181,616

[22] Filed: Apr. 14, 1988

[51] Int. Cl.$^5$ .............................................. A61F 15/16
[52] U.S. Cl. .................................. 604/386; 604/385.1; 604/387
[58] Field of Search ................. 604/389, 385.1, 385.2, 604/386, 397, 398, 387

[56] References Cited

U.S. PATENT DOCUMENTS

| | | | |
|---|---|---|---|
| 2,787,271 | 4/1957 | Clark . | |
| 3,397,697 | 8/1968 | Rickard | 604/370 |
| 4,044,769 | 8/1977 | Papajohn | 604/385.2 |
| 4,285,343 | 8/1981 | McNair | 604/385.1 |
| 4,389,211 | 6/1983 | Lenaghan | 604/383 |
| 4,579,556 | 4/1986 | McFarland | 604/385 A |
| 4,589,876 | 5/1986 | Van Tilburg | 604/385 R |
| 4,608,047 | 8/1986 | Mattingly | 604/387 |
| 4,692,163 | 9/1987 | Widlund et al. | 604/385.2 |
| 4,701,177 | 10/1987 | Ellis et al. | 604/385 A |
| 4,701,178 | 10/1987 | Glaug et al. | 604/387 |
| 4,759,754 | 7/1988 | Korpman | 604/387 |
| 4,911,701 | 3/1990 | Mavinkurve | 604/385.2 |
| 4,917,697 | 4/1990 | Osborn et al. | 604/387 |
| 4,940,462 | 7/1990 | Salerro | 604/387 |
| 5,009,653 | 4/1991 | Osborn | 604/385.1 |

FOREIGN PATENT DOCUMENTS

| | | | |
|---|---|---|---|
| 0091412 | 12/1983 | European Pat. Off. . | |
| 0249924 | 12/1987 | European Pat. Off. | 604/386 |
| 46-612554 | 5/1971 | Japan . | |
| 50-100399 | 8/1975 | Japan . | |
| 2161384 | 1/1986 | United Kingdom | 604/385.1 |

Primary Examiner—C. Fred Rosenbaum
Assistant Examiner—Mark O. Polutta

[57] ABSTRACT

Sanitary napkins are disclosed which include side-protecting flaps having specially designed hinge means for disposing at least one of the flaps in a pre-folded, flexible position. The flap or flaps of the preferred embodiments may be wrapped around a crotch portion of an undergarment without additional attachment adhesive.

15 Claims, 1 Drawing Sheet

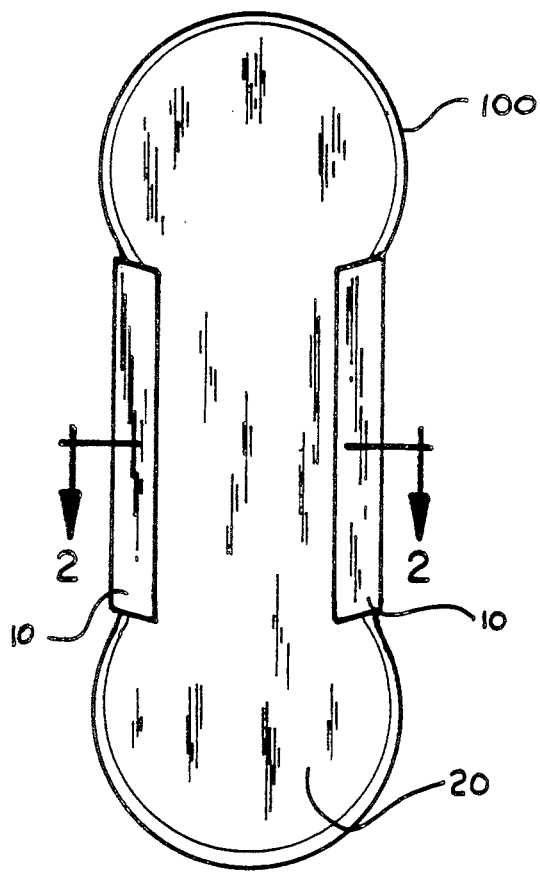
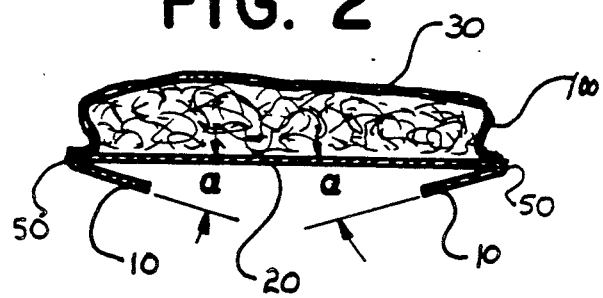
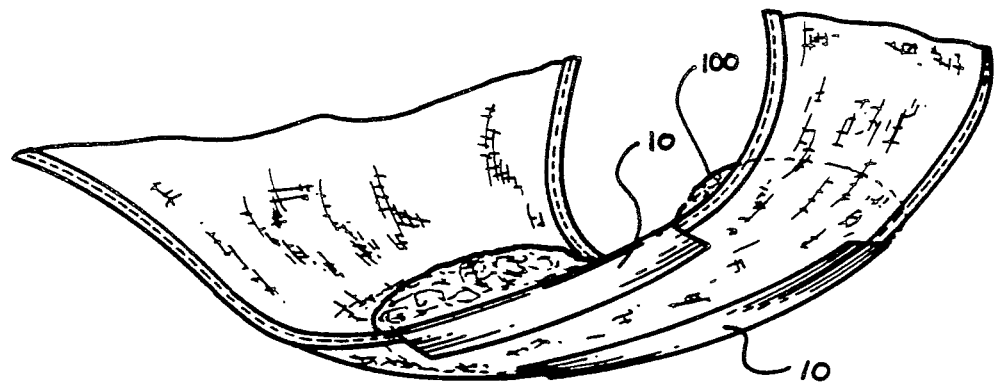

SANITARY NAPKIN HAVING AN ATTACHMENT SYSTEM COMPRISING BIASED HINGES

CROSS REFERENCE TO RELATED APPLICATIONS

This application is related to co-pending application Ser. No. 160,966, filed Feb. 26, 1988 in the name of Pramod Mavinkurve, entitled "Sanitary Napkin Having Elastic Shaping Means", now U.S. Pat. No. 4,911,701, which is assigned to the assignee of this application and which is hereby incorporated by reference.

FIELD OF THE INVENTION

This invention relates to protective, absorbent liners for undergarments and more particularly, to shaping sanitary napkin for folding side panels around the edges of a crotch portion of a panty.

BACKGROUND OF THE INVENTION

The loss of the protection expected of a sanitary napkin product may be caused by a lack of close contact with the body of the wearer, as well as a failure to provide adequate coverage over the requisite area of an undergarment. Those skilled in the art of sanitary protection have attempted to overcome these problems by introducing absorbent products having members disposed longitudinally in order to attempt to create raised edge portions adjacent a central absorbent area. These raised edge barriers are intended to act as barriers against lateral leakage. For example, McFarland, U.S. Pat. No. 4,579,556; Widlund, et al., EPO 0091412, filed Mar. 17, 1983; and Mokry, EPO 0155515, filed Feb. 2, 1985, and Van Tilburg, U.S. Pat. No. 4,589,876 have made attempts to solve failure problems using such means.

Some of the more recent napkin designs, in order to address further the lateral leakage problem, have included side panels, flaps or wings that extend laterally from the longitudinal sides of the central absorbent. Mattingly, U.S. Pat. No. 4,608,047, and McNair, U.S. Pat. No. 4,285,343. These products were designed to protect undergarments by providing side extensions that wrap around the crotch of an undergarment, such as a panty, to prevent body fluids from seeping over the longitudinal sides and staining the panty. The flaps of these napkins preferably have adhesive disposed on their body fluid impervious surfaces for attaching them to an undergarment. The McNair patent, for example, describes the use of adhesive under the central absorbent which is exposed by removing release paper releasably attached to the adhesive. The napkin is then attached to the crotch portion of the undergarment. The user removes the release paper from the adhesive on each of flaps and attaches the flaps to the underside surface of the undergarment. Attaching the flaps in this fashion, however, is known to be a time-consuming and tedious task. The procedure is, moreover, conducive to misplacement of the product.

Accordingly, a need exists for a sanitary napkin having panty protecting flaps which can be adhered to and removed from the panty more conveniently.

It is, therefore, an object of this invention to provide a winged sanitary napkin that is relatively easy to remove after use compared to those of the prior art.

It is another object of this invention to provide a winged sanitary napkin having resilient hinge portions which enable an adhesive-free placement of the flaps around the sides of the crotch portion of a panty.

With these and other objects in view, which will become apparent to one skilled in the art as the description proceeds, this invention resides in the novel construction, combination, arrangement of parts and methods substantially as hereinafter described and more particularly defined in the attached claims.

SUMMARY OF THE INVENTION

Winged sanitary napkins having a body facing surface, an oppositely disposed undergarment facing surface, longitudinal sides and flaps attachably disposed along the longitudinal sides adjacent to a central absorbent element are provided having specially designed hinge means located along at least one longitudinal side. The hinge means serve to dispose at least one flap in a pre-folded flexible position such that the napkin can be attached to the undergarment of a user without requiring positioning adhesive on the flaps. Preferably, the napkins of this invention have flaps which form a sufficiently acute angle with the undergarment facing side of the central absorbent element to allow the flaps to overlap a side of a crotch portion of the undergarment.

The products of this invention are first attached to a panty with positioning adhesive. The flaps of the products are then unfolded to allow the crotch of the panty to fit to the adhesive-coated, garment-facing side of the napkin between the flaps.

The attachment systems provided by this invention minimize the staining of the panty due to increased undergarment coverage by the flaps which wrap around the crotch of the undergarment. The products of this invention also have the advantage of increasing discretion, by eliminating release paper which otherwise would need to be discarded. In preferred embodiments of this invention, the body facing side of the flanges have some absorbent capacity, while the undergarment facing side of these flaps can be made with a body fluid-impervious material.

BRIEF DESCRIPTION OF THE DRAWINGS

The accompanying drawings illustrate a complete embodiment of the invention according to the best mode for the best practical application of the principles thereof, and in which:

FIG. 1: is a planar view of the undergarment facing side of a sanitary napkin embodiment of this invention illustrating the flaps disposed to form angles with the undergarment facing side of the napkin;

FIG. 2: is a transverse cross-sectional view, taken through line 2—2 of FIG. 1, illustrating the preferred acute angles formed by the flaps and the undergarment facing side of the napkin's absorbent element;

FIG. 3: is a perspective view of the application of the sanitary napkin of FIG. 1 disposed onto a crotch portion of an undergarment.

DESCRIPTION OF THE INVENTION

With reference to the drawings, and particularly FIGS. 1 and 2 thereof, there is shown a preferred sanitary napkin 100 having an absorbent element with longitudinally extending sides, transverse ends, a body-facing side 30 and an undergarment facing side 20. Flaps 10 of this embodiment extend laterally from each of the longitudinal sides of the absorbent element and at least one of these flaps comprises a hinge means for disposing said flap or flaps in angular relation to the undergarment facing side 20 of the absorbent element. Preferably, both of the flaps include hinge means, which enable both flaps to overlap a corresponding side portion of the crotch of an undergarment.

Hinge means 50 can be used to dispose the flaps 10 in angular relation to the undergarment facing side 20 of the absorbent element in angles of less than 90, 45, 30 and, most preferably, less than 15 degrees. The hinge means of this invention can be formed from a variety of resilient materials, or materials which can be made resilient via heat treatment, mechanical or chemical means. In one preferred embodiment, the hinge means comprises a resilient polymeric material, preferably a bicomponent fiber, such as Enka TM, in combination with a Hollofil TM polyester product or similar polyester containing fiber material. The hinge means can also comprise other thermoplastic materials, such as Volara TM (type E) from Voltex, Inc. Most Preferably, the chosen material is heat cured and compressed Enka TM -Hollofil TM the material in which the components are present in a 1:1 ratio. Heat curing and compression serve to obtain the desired angular configuration. The hinge means of this invention may be integral with flaps along the longitudinally extending sides or they may be of separate construction.

Alternatively, a biased hinge for this invention by introducing elastic strip materials, preferably disposed on the body fluid impervious surface. These strips can be arranged transversely across the flaps and the central absorbent element, so as to provide a "hinging effect" to the flaps 10. One preferred design illustrative of this concept is an example employing laterally disposed elastic strips of Fullastic TM material by Fuller, Inc. The hinge means of this invention may also be made by incorporating one or more thin metal or bendable plastic wires transversely across the flaps and central absorbent element and bending it to the desired angle.

Pressure sensitive attachment adhesive may, optionally, be applied to undergarment facing side of the sanitary napkins of this invention. Attachment adhesives are well known to those of skill in the art. Preferably, such adhesive is applied in strips along the longitudinal axis of the undergarment facing side of the sanitary napkin. Such adhesive is, preferably, sufficiently strong to adhere to the undergarment, but not so strong that it cannot be removed from the undergarment when the sanitary napkin is removed.

Adhesive compositions suitable for sanitary napkins, include, for example, water-based, pressure-sensitive adhesives such as acrylate adhesives. Alternatively, the adhesive may comprise rapid setting thermoplastic "hot-melt", rubber adhesives, or two-sided adhesive tape. As is customary in the art, a preferred kraft paper release strip can also be applied to these adhesive compositions to protect them prior to use.

The napkins of this invention can be disposed onto an undergarment by folding the flaps 10 over a crotch portion of an undergarment and adhering strips of attachment adhesive. The flaps are folded over the undergarment by laterally extending them and then allowing them to fold over the crotch portion of the undergarment.

The absorbent element can contain resilient material known to those of skill in the art for enabling napkin 100 to bend easily without excessive distortion. Such materials include compacted cellulosic fibers and hydrocolloidal material such as those described by Kopolow, U.S. Pat. No. 4,551,142, which is herein incorporated by reference. The preferred absorbent element can be approximately 4–12 inches long, preferably about 8–11 inches. It may contain a core, preferably made of loosely associated absorbent hydrophilic materials such as cellulose fibers, wood pulp, regenerated cellulose or cotton fibers, a blend of pulp and other resilient fibers including fibers which are fluid repellant, and/or other materials generally known in the art. The absorbent element may be either rectangular or shaped.

As is customary in the art, the body-facing side of napkin 100 is a body fluid pervious surface. Such body fluid pervious surfaces can be made of relatively non-absorbing fluid-pervious material. This material provides increased comfort and conformability and directs fluid to an underlying layer, for example, wood pulp, which retains such fluid. Furthermore, the body fluid pervious surface should retain little or no fluid in its structure to provide a relatively dry surface next to the skin. Preferably, the body fluid pervious surface is a single, rectangular sheet of material having a width sufficient to cover the body-facing side of the absorbent element. Preferably, the body fluid Pervious surface is longer than the absorbent element so as to form end tabs, which may be sealed with other pervious or non-pervious layers to fully enclose the absorbent element. This surface may be woven or non-woven material which can be penetrated by body fluid. The fluid pervious surface is preferably made of fibers or filaments of thermoplastic polymers such as polyethylene or polypropylene or apertured polymeric film.

Underlying the absorbent element may be another layer of absorbent material to provide additional resiliency to the product. This layer may extend beyond the longitudinal sides of the absorbent core to entrap any body fluid which escapes from the sides of the absorbent element. This layer may also be substantially wider than the core of the absorbent element and may extend into the flaps. The absorbent layer may comprise a thin, absorbent layer of material such as tissue, fabric, or the like, made of cellulosic fibers. Because such material is provided as a safety measure and is only required in order to contain escaped fluid, it need not be extremely absorbent, and, in fact, may be composed of a capillary or cellular system, including hydrophobic material and the like. However, the preferred material is a hydrophilic fabric comprised of cellulosic fibers such as wood pulp tissue or other suitable hydrophilic woven or non-woven material. This preferred tissue has the advantage of providing resiliency and conformability to the product.

The sanitary napkins of this invention can further include a body-fluid impervious surface on the undergarment-facing side. Such an impervious surface will, preferably, permit passage of air and moisture vapor to the outer surface while blocking the passage of fluid. The impervious surface may be fastened to a core or absorbent element, or to a core wrapped in a pervious surface cover by heat sealing or by adhesive. The impervious surface may be made of any thin, flexible, body fluid impermeable material such as a polymeric film, for example, polyethylene, polypropylene, cellophane or even a normally fluid pervious material that has been treated to be impervious, such as impregnated fluid repellent paper or non-woven fabric material. Most preferably, the impervious surfaces include a plastic film of polyethylene or a bicomponent film such as an ethylvinylacetate/polyethylene coextruded film.

The preferred expandable flap 10 of this invention should be made of a stretchable, flexible material. Preferably, flap 10 does not contain absorbent pulp materials. Flap 10 may also include a body fluid impervious backing such as the materials described above in connection with the body fluid-impervious surfaces for the undergarment facing side of the absorbent core. Flap 10 may have a body fluid pervious cover, and absorbent tissue disposed between the cover and backing layers. In addition, flaps 10 of this invention preferably contain absorbent tissue with sufficient capillary action to retain small quantities of liquid. This tissue can be heat sealed or adhesively sealed around the edges of the flap 10 with the preferred impervious backings and body fluid pervious covers of the flaps 10 to form absorbent areas. The flaps can, therefore, act as body fluid reservoirs to aid in preventing failures.

From the foregoing it can be realized that this invention provides facilitated application of winged sanitary napkins. Flexible hinge means are readily expanded during application and enable the flaps to lie comfortably around the crotch of the wearer's undergarment without the inconvenience of additional adhesive placement. Although various embodiments have been illustrated, this was for the purpose of describing, but not limiting, the invention. Various modifications, which will become apparent to one skilled in the art, are within the scope of this invention described in the attached claims.

We claim:

1. A sanitary napkin comprising:
   (a) an absorbent element having longitudinally extending sides, transverse ends, a body-facing side and an undergarment facing side; and
   (b) flaps extending laterally from each of said longitudinal sides of said absorbent element, said flaps having proximal and distal portions in relation to said longitudinal sides of said absorbent element disposing said distal portion of said flap in acute angular relation with said undergarment facing side of said absorbent element.

2. A sanitary napkin of claim 1 wherein both of said flaps comprise hinge means for disposing said flaps in angular relation with said undergarment facing side of said absorbent element.

3. The sanitary napkin of claim 1 wherein said flap is disposed to form an angle sufficiently acute to wrap around a side of a crotch portion of an undergarment.

4. The sanitary napkin of claim 3 wherein said angle is less than about 90°.

5. The sanitary napkin of claim 3 wherein said angle is less than about 45°.

6. The sanitary napkin of claim 3 wherein said angle is less than about 30°.

7. The sanitary napkin of claim 3 wherein said angle is less than about 15°.

8. The sanitary napkin of claim 4 wherein said hinge means comprises a resilient polymeric material.

9. The sanitary napkin of claim 8 wherein said resilient polymeric material comprises a thermoplastic fiber.

10. The sanitary napkin of claim 9 wherein said resilient polymeric material comprises hollow polyester fibers.

11. The sanitary napkin of claim 8 wherein said resilient polymeric material is heat cured and compressed and resiliently set to form said angle.

12. A method of applying a sanitary napkin to an undergarment, comprising:
    (a) providing a sanitary napkin having an absorbent element having longitudinally extending sides, transverse ends, a body-facing side and an undergarment facing side, said napkin further including flaps extending laterally from each of said longitudinal sides of said absorbent element, said flaps having proximal and distal portions in relation to said longitudinal sides of said absorbent element, said flaps comprising resilient hinge means disposed between at least one of said longitudinally extending sides of said absorbent element and the distal portion of one of said flaps, said resilient hinge means disposing the distal portions of each of said flaps in angular relation with said undergarment facing side of said absorbent element;
    (b) disposing said undergarment facing side of said sanitary napkin onto said undergarment; and
    (c) folding said flaps over a crotch portion of said undergarment whereby said flaps are laterally extended prior to allowing them to fold over an outside portion of said undergarment.

13. The method of claim 12 wherein said providing step provides flaps disposed to form an angle with said undergarment facing side of said absorbent element of less than about 45°.

14. The method of claim 12 wherein said providing step provides flaps disposed to form an angle with said undergarment facing side of said absorbent element of less than about 15°.

15. The method of claim 12 wherein said providing step provides a hinge means comprising a heat treated thermoplastic.

* * * * *

UNITED STATES PATENT AND TRADEMARK OFFICE
CERTIFICATE OF CORRECTION

PATENT NO. : 5,125,918
DATED : June 30, 1992
INVENTOR(S) : Wassim Seidy

It is certified that error appears in the above-identified patent and that said Letters Patent is hereby corrected as shown below:

Claim 1, column 5, lines 36-42 should read:

-- (b) flaps extending laterally from each of said longitudinal sides of said absorbent element, said flaps having proximal and distal portions in relation to said longitudinal sides of said absorbent element said flaps comprising at least one of said longitudinally extending sides of said absorbent element and the distal portion of one of said flaps, said resilient hinge means disposing said distal portion of said flap in acute angular relation with said undergarment facing side of said absorbent element. --

Signed and Sealed this

Twenty-fourth Day of August, 1993

Attest:

BRUCE LEHMAN

Attesting Officer        Commissioner of Patents and Trademarks